(12) United States Patent
Caussette et al.

(10) Patent No.: US 9,182,397 B2
(45) Date of Patent: Nov. 10, 2015

(54) IMMUNOASSAY FOR DETECTING ANTIBIOTICS

(75) Inventors: Mylene Patrice Dominique Caussette, AC Echt (NL); Stephen Ludovic Alexandre Hennart, AC Echt (NL); Maartje Maria Franse, AC Echt (NL)

(73) Assignee: DSM IP ASSETS B.V., Heerlen (NL)

(*) Notice: Subject to any disclaimer, the term of this patent is extended or adjusted under 35 U.S.C. 154(b) by 0 days.

(21) Appl. No.: 14/344,204

(22) PCT Filed: Sep. 13, 2012

(86) PCT No.: PCT/EP2012/067944
§ 371 (c)(1),
(2), (4) Date: Mar. 11, 2014

(87) PCT Pub. No.: WO2013/037885
PCT Pub. Date: Mar. 21, 2013

(65) Prior Publication Data
US 2014/0342376 A1 Nov. 20, 2014

(30) Foreign Application Priority Data

Sep. 16, 2011 (EP) ..................................... 11181581
Jul. 18, 2012 (EP) ..................................... 12176912

(51) Int. Cl.
*G01N 33/569* (2006.01)
*G01N 33/558* (2006.01)
*G01N 33/543* (2006.01)

(52) U.S. Cl.
CPC ........ *G01N 33/569* (2013.01); *G01N 33/54386* (2013.01); *G01N 33/558* (2013.01); *G01N 2415/00* (2013.01); *G01N 2458/00* (2013.01)

(58) Field of Classification Search
CPC . G01N 33/558; G01N 33/86; G01N 2415/00; G01N 2458/00; G01N 33/54386; G01N 33/721
USPC ............. 435/13, 287.1, 287.2, 7.1, 28, 287.8, 435/29, 5, 7.32
See application file for complete search history.

(56) References Cited

U.S. PATENT DOCUMENTS 3,850,787 A 11/1974 Robinson et al.
5,434,053 A * 7/1995 Piasio ............................ 435/7.9

FOREIGN PATENT DOCUMENTS

| CN | 101633948 A | 1/2010 |
|---|---|---|
| EP | 0593112 A1 | 4/1994 |
| EP | 0755456 B1 | 1/1997 |
| IL | 40258 A | 4/1977 |
| WO | 9638720 A1 | 12/1996 |
| WO | 9706439 A1 | 2/1997 |
| WO | 9967416 A2 | 12/1999 |

OTHER PUBLICATIONS

Analytica Chimica Acta 2009, vol. 634, No. 1, pp. 129-133.*
International Search Report corresponding to PCT/EP2012/067944 mailed Nov. 21, 2012.

* cited by examiner

*Primary Examiner* — Padma V Baskar
(74) *Attorney, Agent, or Firm* — Miles & Stockbridge PC (57) ABSTRACT

The present invention relates to a device and method for detecting analytes in a sample.

13 Claims, 1 Drawing Sheet

IMMUNOASSAY FOR DETECTING ANTIBIOTICS

CROSS REFERENCE TO RELATED APPLICATIONS

This application is a §371 National Stage Application of PCT/EP2012/067944, filed Sep. 13, 2012, which claims priority to European Application No. 12176912.9, filed Jul. 18, 2012, which claims priority to European Application No. 11181581.7, filed Sep. 16, 2011.

BACKGROUND OF THE INVENTION

1. Field of the Invention

The present invention discloses a device and method for detecting analytes in a sample.

2. Description of Related Art

Antibiotics are used for combating infectious diseases, both in humans and in animals. It is well known that misuse of antibiotics such as administration of antibiotics whenever this is not required from a medical point of view or incomplete courses of treatment is the most important cause of the development of antibiotic resistance. Thus, methods for detecting the presence of antibiotics in samples such as e.g. milk, blood, fish, feed, meat, serum, urine, water and the like are of utmost importance in the prevention of the unwanted spread of antibiotics. In many areas, this process of detection can only be performed adequately, if a fast and simple test is available. In general, there are two types of tests suitable for routinely monitoring the presence of antibiotics in samples. Firstly, there are microbial inhibition tests, wherein a test microorganism is contacted with the sample to be tested and the growth (or inhibition of growth) of the microorganism is observed, for instance with the use of an indicator. An example of such a test is described in EP 0 755 456 B1. The major drawback of microbial inhibition tests is that it takes a relatively long time to obtain results.

Secondly, there are competitive immunoassays, wherein the antibiotic to be tested and a reference antibiotic present in the test compete for binding with binding proteins and/or antibodies with affinity for the antibiotics. Visualization is usually done by means of labeling. One of many examples of such a test is described in EP 0 593 112 B1. Although these types of tests are in general faster than microbial inhibition tests, they still require extensive handling by the end user and are therefore not user friendly.

In view of the above, it is clear that there exists considerable room for improvement in the area of antibiotic testing, particularly where it concerns to ease-of-use, speed and convenience.

SUMMARY

There is a wide range of applications for the methods, test devices and kits according to the present invention across the entire field of diagnostics and analysis. They can be used to detect any type of analyte in a sample, including antibiotics, carbohydrates, dietary substances, microorganisms, (poly)nucleotides, (poly)peptides, steroids, hormones, toxins, (agro)chemical agents such as fungicides, herbicides and pesticides, vitamins, drugs, metabolites, receptors, antibodies, allergens, to name just a few. In a preferred embodiment the methods, test devices and kits according to the present invention are used to detect antibiotics in a sample.

The term 'antibiotic' as used herein refers to one or more substances or chemical constituents (or metabolites of such substances or chemical compounds) of a sample that display activity against bacteria. In an embodiment of the invention the antibiotic to be detected by the method, test device and/or kit according to the present invention is selected from the group consisting of the family of beta-lactam antibiotics, the family of tetracycline antibiotics, the family of sulfonamide antibiotics, the family of aminoglycoside antibiotics, and the family of quinolone antibiotics. In a preferred embodiment of the invention the antibiotic to be detected by the method, test device and/or kit according to the present invention is a beta-lactam antibiotic. The term 'beta-lactam antibiotic' refers to compounds (or metabolites thereof) that comprise a beta-lactam substructure within their chemical structure and display activity against bacteria. Two important subclasses of the beta-lactam antibiotics are the cephalosporin-derived antibiotics and the penicillin-derived antibiotics. Examples of the cephalosporin-derived antibiotics are cefaclor, cefadroxil, ceftiofur, cephalexin, cephapirin and cephradine. Examples of the penicillin-derived antibiotics are amoxicillin, ampicillin, cloxacillin, dicloxacillin, flucloxacillin, oxacillin, penicillin G, penicillin V and ticarcillin.

The present invention relates to a method for detecting an antibiotic in a sample, said method comprising the steps of:

a) contacting a liquid sample with a labeled antibiotic binding protein and a labeled control reagent to form a liquid composition, b) providing a test device having a proximal and a distal end, said test device configured to allow lateral flow from the proximal to the distal end, said test device comprising a solid support comprising the following regions in sequence from the proximal to the distal end:

i. a sample receiving region, ii. a detection region, said detection region comprising at least two zones:

A. a detection zone comprising an immobilized antibiotic capable of binding the labeled antibiotic binding protein, when said labeled antibiotic binding protein is unbound by antibiotic from the sample, and B. a control zone comprising an immobilized binding agent capable of binding the labeled control reagent, iii. a absorbing region, and iv. optionally, a handling region, c) contacting the liquid composition with the sample receiving region of the test device, d) allowing the liquid composition to move from the sample receiving region through the detection region to the absorbing region, so as to allow the liquid composition comprising the labeled antibiotic binding protein and the labeled control reagent to contact the detection zone and the control zone, e) detecting a signal at the detection zone and a signal at the control zone, wherein i. the absence of antibiotic in the sample is indicated by the presence of a signal at the detection zone that is more intense than the signal at the control zone, and ii. the presence of antibiotic in the sample is indicated by the absence of a signal at the detection zone or the presence of a signal at the detection zone that is less intense than the signal at the control zone.

DETAILED DESCRIPTION OF PREFERRED EMBODIMENT

Figure 1:
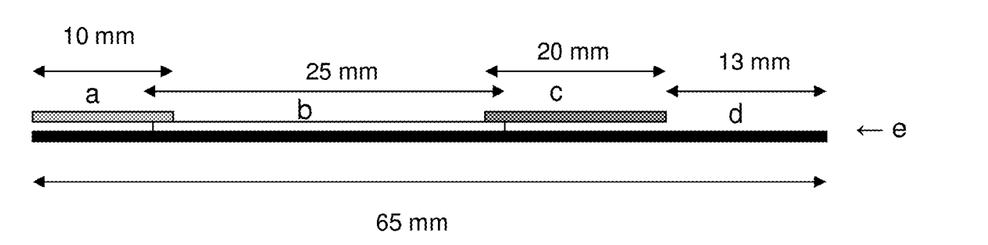
FIG. 1 is a side view of an embodiment of the test device according to the present invention. The test device comprises a solid support (e) comprising a sample receiving region (a), a detection region (b), an absorbing region (c) and a handling region (d).

In a first step the sample is contacted with at least one labeled antibiotic binding protein and at least one labeled control reagent. In an embodiment the sample may be contacted with more than one labeled antibiotic binding protein and/or more than one labeled control reagent. The labeled antibiotic binding protein and the labeled control reagent can be present in liquid or solid form before they are contacted with the sample. Both agents may be in liquid form, or both agents may be in solid form, or one agent may be in solid form and the other agent may be in liquid form. Preferably, both agents are present in solid form, preferably in powder form. The solid form can be made by drying or lyophilizing the compounds. The powder can be resuspended in the sample. If necessary, the obtained liquid composition can be mixed (by e.g. applying vortices) to improve and/or fasten resuspension of the powder in the sample. If desired, compounds facilitating resuspension and/or dissolution and/or mixing of the labeled antibiotic binding protein, the labeled control reagent and the sample can be added. In a preferred embodiment these compounds are present with the labeled antibiotic binding protein and the labeled control reagent before they are contacted with the sample. Preferably, these compounds are also in solid form e.g. in powder form. Suitable compounds include, but are not limited to, a buffer e.g. an organic buffer such as a Tris buffer, a surfactant such as Triton X-100, a protein such as bovine serum albumin, a polyol such as glycerin, and a sugar e.g. a disaccharide such as saccharose. In an embodiment the amount of the liquid sample added to the antibiotic binding protein and the labeled control reagent is between 50 and 1000 µl, preferably between 75 and 7500 µl, more preferably between 100 and 500 µl, in particular between 125 and 250 µl. After the sample is contacted with at least one labeled antibiotic binding protein and at least one labeled control reagent, the obtained liquid composition may be shaken. Shaking is generally done for 1 to 20 seconds, preferably 5 to 15 seconds with about 10 seconds being preferred.

In an embodiment the labeled antibiotic binding protein and the labeled control reagent are present in a container. Preferably, the above compounds are also present in the container. The labeled antibiotic binding protein and the labeled control reagent may be present in different containers, but preferably they are present in one container. Containers that can be used in the present invention may be tubes of any shape and size and from any suitable material available. Containers may also be the wells such as those incorporated in microtiter plates. In a preferred embodiment the container comprises the labeled antibiotic binding protein, the labeled control reagent, a buffer e.g. an organic buffer such as a Tris buffer, a surfactant such as Triton X-100 (preferably in a concentration of between 0 and 0.1% w/v), a protein such as bovine serum albumin, a polyol such as glycerin, and a sugar e.g. a disaccharide such as saccharose.

Alternatively, the labeled antibiotic binding protein and the labeled control reagent are part of the test device, for example they can be present in liquid or solid form in the sample receiving region or in a separate region located in front of the sample receiving region or between the sample receiving region and the detection region. In this embodiment rather than add a pre-measured volume into the container, the test device might be arranged to be dipped into the fluid sample to absorb the selected amount of sample.

In an embodiment the sample might be solid and liquid comprising the antibiotic(s) needs to be extracted from the sample. Methods for extracting liquids from samples are dependent on the type of sample. Suitable extraction methods for different types of samples are known to the person skilled in the art and include disintegration of the solid sample by homogenization, vortexing with beads, grinding or sonication and/or solvent extraction. In a preferred embodiment the sample that is contacted with the labeled antibiotic binding protein and the labeled control reagent is liquid. In an embodiment of the invention the sample may be derived from a body liquid, an organ, meat or eggs. Antibiotics might also be present in food products in which these animal products are added as an ingredient. Examples of food products are milk; honey; meat of cow, pig, poultry and fish; sea food such as shrimps; processed meat products such as sausages; ready-to-eat meals; feed; and baby food. Antibiotics might also be present in body liquids or animal tissues, which are suitable for examination by for example food inspection authorities. Examples are blood, liver tissue, muscle tissue, heart tissue, kidney tissue or pre-urine obtained from the kidney and urine. Urine and blood are suitable for examination prior to slaughtering of an animal. Antibiotics may also be present in water such as waste water. In a preferred embodiment the sample is milk. The milk may be obtained from cattle (e.g. cows), horses, sheep, goats, yaks, water buffalo, humans, donkeys, reindeers, bison and camels. Antibiotics may also be present in semi-processed or processed food such as pasteurized products, UHT-products, skimmed or partially skimmed milk, whey, fresh or ripened cheese, yoghurt, cream, butter, sour cream, buttermilk, to name just a few.

In an embodiment the liquid composition (i.e. the liquid composition obtained in step a) is incubated for 30 seconds to 5 minutes, preferably 45 seconds to 4 minutes, more preferably 50 seconds to 3 minutes, most preferably 55 seconds to 2.5 minutes and in particular 1 to 2 minutes before the liquid composition is contacted with the test device. The liquid composition is incubated at a temperature of between 40 and 70° C., preferably a temperature of between 50 and 65° C., more preferably a temperature of between 60 and 64° C. In an embodiment, the liquid composition obtained in step a is incubated after shaking. In another embodiment, shaking is done after incubation of the liquid composition obtained in step a. In yet another embodiment, shaking is done before and after incubation. Shaking time before and after incubation may be equal, but may also differ.

In a preferred embodiment incubation continues after the liquid composition is contacted with the test device. In an embodiment the test device is contacted with the liquid composition for 1 to 5 minutes, preferably 1.5 to 4 minutes, more preferably 2 to 3 minutes at a temperature of 40 to 70° C., preferably a temperature of between 50 and 65° C., more preferably a temperature of between 60 and 64° C. Incubation can be carried out with the aid of a thermostatic device such as a water bath or an incubator. In a preferred embodiment the temperature before and after the liquid composition is contacted with the test device is identical. Incubation may be stopped as soon as a signal is detected at the detection zone and/or the control zone.

The labeled antibiotic binding protein may be any protein capable of binding to the antibiotic to be detected. The binding protein may bind a family of antibiotics which have similar structural binding sites. Suitable binding proteins include, but are not limited to, antibodies (monoclonal, polyclonal or recombinant), antibody fragments, enzymes, aptamers, and receptors such as penicillin binding protein. Preferably, the antibiotic binding protein is a protein obtained from a microorganism. In an embodiment the microorganism is an antibiotic sensitive microorganism. In an embodiment of the invention the organism is selected from the group consisting of a *Bacillus* species, an *Escherichia* species and a *Streptococcus* species. In a preferred embodiment of the invention the organism is thermophilic. Examples are *Bacillus stearothermophilus* or *Streptococcus thermophilus*, with *Bacillus stearothermophilus* being preferred.

The labels of the antibiotic binding protein and the control reagent may be different, but in a preferred embodiment they are identical. Visible as well as non-visible labels can be used. Suitable labels include, but are not limited to, fluorescent compounds, chromogenic compounds, chemiluminescent compounds, radioactive compounds, colorimetric compounds, magnetic compounds (e.g. beads or particles), enzymes, catalytic compounds, substrates, vesicles with labels and particles such as dye particles, colored latex particles, carbon particles, metallic particles, non-metallic particles, colloidal metallic particles. In a preferred embodiment the labels are visible labels with colloidal metallic particles being preferred and gold particles, e.g. colloidal gold particles, being most preferred. The label may be bound to the antibiotic binding protein and/or the control reagent by any suitable means including conjugation, covalent bonding or non-covalent bonding. The label may be directly bound to the antibiotic binding protein and/or the control reagent or the label may be bound through a conjugate such as a biotin-streptavidin conjugate or a biotin-avidin conjugate.

In an embodiment the control reagent is unable to bind to the antibiotic in the sample. In an embodiment the control agent forms a specific binding pair with the binding agent immobilized in the control zone of the detection region of the test device. The term 'specific binding pair' as used herein refers to two substances that specifically bind to each other.

In an embodiment the test device is a test strip. In view of the small volumes of liquid sample added to the labeled antibiotic binding protein and the labeled control reagent, it is recommended that the test device is placed such that it rests in the angle between bottom and wall.

In the method of the present invention, when the label density (i.e. signal) in the detection zone is higher than that in the control zone, the sample contains no antibiotic or antibiotic at a concentration below a given threshold (in other words, the antibiotic is not present in a sufficient amount and the test is considered 'negative'). Ergo, when in the present application is referred to "the absence of antibiotic in the sample", it is meant that the sample contains no antibiotic or antibiotic at a concentration below a given threshold. However, when the label density in the detection zone is less than the label density in the control zone, antibiotic is present in the sample at a concentration above a given threshold (in other words, the antibiotic is present in an amount in excess of allowable levels and the test is considered 'positive'). Ergo, when in the present application is referred to "the presence of antibiotic in the sample", it is meant that the sample contains antibiotic at a concentration above a given threshold. When the label density (i.e. signal) in the detection zone is equally intense as the label density (i.e. signal) in the control zone, antibiotic is present in the sample at a concentration above, at or below a given threshold. This depends on the chosen threshold. 'Threshold' as used herein refers to the concentration value above which a given antibiotic is to be regarded as present and below which said antibiotic is to be regarded as absent. Generally, a threshold value is given for particular antibiotics in particular samples by local, regional or interregional authorities, but it can also be pre-set for certain research purposes. The signals may be detected visually by eye, but also by means of a signal reading device such as e.g. a spectrophotometer, a reflectance reader, a fluorometer, a camera, a magnetic detector, a scintillation counter, to name just a few.

The intensity of the detectable label at the detection zone can be measured to determine the result of the method of the present invention. The method of the present invention may provide a yes or no result (i.e. antibiotic present or absent) or may determine the presence or absence of an antibiotic above or below a certain threshold value (which is in fact also a yes or no result). The intensity of the signal can be inversely related to the concentration of antibiotic in the sample. Furthermore, the intensity of the signal at the detection zone can be compared to the intensity of the signal at the control zone to determine a result of the method of the present invention. The difference between the intensities of the various zones can even be analyzed by a signal reading device and used to calculate the concentration of antibiotic in the sample, for example by comparing the result to a predetermined value.

The invention further relates to a test device for detecting an antibiotic in a sample, said test device having a proximal and a distal end, said test device configured to allow lateral flow of a liquid composition comprising a liquid sample, a labeled antibiotic binding protein and a labeled control reagent from the proximal to the distal end, said device comprising a solid support comprising the following regions in sequence from the proximal to the distal end:
  a sample receiving region,
  a detection region, said detection region comprising at least two zones:
    i. a detection zone comprising an immobilized antibiotic capable of binding the labeled antibiotic binding protein, when said labeled antibiotic binding protein is unbound by antibiotic from the sample, and
    ii. a control zone comprising an immobilized binding agent capable of binding the labeled control reagent,
  an absorbing region, and
  optionally, a handling region.

'Solid support' as used herein refers to material that is used to provide support for the various regions of the test device. When used for a test device according to the present invention, a solid support usually is made from material that is inert with respect to the application for which the test device is to be used. Suitable materials are glass, metals, and various types of plastics such as for instance polystyrene. The solid support may have a thickness of between 0.1 and 1 mm. In an embodiment the test device may be housed within a non-absorbent or laminate casing. In other words, the test device includes a housing defining an elongated cavity for receiving and holding the test device. Suitable housings are known to a person skilled in the art.

Attachment of the regions to the backing can be performed following known techniques such as gluing, thermo compression and the like.

The test devices of the present invention usually has a length varying between 10 and 200 mm, preferably between 20 and 150 mm, more preferably between 30 and 100 mm, and in particular between 50 and 75 mm, a width varying between 1 and 20 mm, preferably between 2 and 15 mm, more preferably between 3 and 10 mm, and a thickness varying between 0.05 and 2 mm, preferably between 0.075 and 1.5 mm, more preferably between 0.1 and 1 mm.

The test devices of the present invention have a shelf-life of at least 6 months, preferably of at least 9 months when stored at 4° C. In another embodiment, the test devices of the present invention have a shelf-life of up to 10 days, preferably up to 20 days and more preferably up to 28 days when stored at −20° C. In yet another embodiment, the test devices of the present invention have a shelf-life of up to 1 day, preferably up to 4 days and more preferably up to 7 days when stored at 30° C. "Shelf-life" as used herein means that the sensitivity of the stored test device does not decrease. Ergo, the sensitivity of a stored test device is equal to the sensitivity of a freshly prepared test device.

In an embodiment the test device can be stored at a temperature of between −20° C. and 30° C. Preferably, the test device is stored at a temperature of between 4° C. and 8° C.

'Sample receiving region' as used herein refers to the portion of the test device which is brought into direct contact with the liquid composition. In other words, the sample receiving region is the portion of the test device which is brought into direct contact with the liquid sample after the liquid sample has been contacted with the labeled antibiotic binding protein and the labeled control reagent. If desired, the sample receiving region may comprise a labeling reagent capable of binding to the antibiotic binding protein and/or the control reagent, particularly in case when the antibiotic binding protein and/or the control reagent are present in unlabeled form when they are contacted with the liquid sample. The sample receiving section is made of porous material. In a preferred embodiment the sample receiving region is made of a material having a pore size of 3-8 μm. Preferably, the sample receiving region is a polyvinyl alcohol-bound glass fibre membrane such as a VF2 membrane.

'Detection region' as used herein refers to the portion of the test device which is in lateral flow contact with the sample receiving region and the absorbing region. The contact can be an end-to-end connection, but preferably there is overlap between the detection region and the sample receiving region and between the detection region and the absorbing region. The overlap may be between 1 and 2 mm. The detection region is made of porous material. Preferably, the detection region is a HF90 membrane. The detection region usually comprises one or more zones, for instance, a detection zone for detecting the presence or absence of the antibiotic and a control zone that functions as a control site. The detection region may also have two or more detection zones and/or two or more control zones. The detection zones may have the same functionality or may have different functionalities (i.e. the capture reagents at the different detection zones may be capable of binding to the same compound or may be capable of binding to different compounds). The same holds true for the control zones. The one or more zones may be made of a porous material different than that of the detection region. The separate zones may be made of a different porous material. Preferably, they are made however of the same material. Preferably, the one or more zones are made of the same material as the detection region. When the liquid composition moves through the detection region, it may first be contacted with the detection zone and then be contacted with the control zone or vice versa. In case the detection region has several detection zones and/or control zones, any sequence of zones may be provided. The zones can be in a variety of configurations including lines, dots or other configurations. In a preferred embodiment the zones are lines.

'Lateral flow' as used herein refers to liquid flow of a sample in a material in which all of the dissolved and/or dispersed components of the sample are transported at essentially equal velocities and with relatively unimpaired flow laterally through the material.

The detection zone and the control zone each may comprise at least one capture reagent. Preferably, the detection zone and control zone are made by applying the appropriate capture reagent or mixture of capture reagents to the detection region, either by means of covalent linkages or other bonding processes. 'Capture reagent' as used herein refers to any reagent that can be used to create the required functionality in the detection and/or control zone. The application of the capture reagent to the detection region can be done by known methods such as spraying, dispensing, painting, drawing, printing, striping and the like. The zones are capable of generating a signal, for instance a visual color signal, upon presence or absence of the complex between the capture reagent and its binding partner.

A capture reagent may be any natural or non-natural compound. Examples of suitable capture reagents are antibiotics, antibodies, antigens, ligands, proteins, to name just a few. In a preferred embodiment the capture reagent at the detection zone of the test device according to the present invention is an antibiotic or an analogue thereof. In a preferred embodiment the antibiotic is immobilized at the detection zone at a concentration of 1-3 mg/mm. Preferably, the antibiotic is present in a Tris buffer when immobilized to the detection zone. Examples of suitable antibiotics or analogues thereof are beta-lactam antibiotics, e.g. cephalosporins such as for instance 7-amino-cephalosporanic acid (7ACA). Preferably, the antibiotic is immobilized on the test device and is capable of binding to the labeled antibiotic binding protein when said labeled antibiotic binding protein is unbound by antibiotic from the sample. When the labeled antibiotic binding protein is bound by antibiotic from the sample, the immobilized antibiotic will not be able to bind to the labeled antibiotic binding protein.

In a preferred embodiment the capture reagent at the control zone of the test device according to the present invention is a member of a binding pair e.g. a specific binding pair such as an antigen/antibody pair. It may however also be an antibody binding protein such as e.g. protein A. The capture agent may be present in a solution comprising an additional protein e.g. bovine serum albumin, a sugar e.g. a disaccharide such as saccharose and a salt such as NaCl when applied to the control zone. In a preferred embodiment the capture agent at the control zone is unable to bind to the antibiotic in the sample and/or the labeled antibiotic binding protein, irrespective of whether the protein has antibiotic bound or not.

Immobilization of the capture reagent to the detection region may be carried out in a manner known per se, for example by covalent or non-covalent adsorption to the detection region. The capture reagent may also be covalently conjugated to the detection region through a carrier such as for instance bovine serum albumin (BSA). Optionally, the capture reagent may be coupled to the carrier via a spacer. Many bifunctional compounds are suitable as a spacer. All methods available to construct bonds, e.g. coupling techniques for instance those known from peptide chemistry, could be applied, unless they are detrimental to the capture reagent. Suitable spacers, carriers and coupling techniques are well known to the person skilled in the art.

The control zone produces a signal irrespective of whether or not an antibiotic is present in the sample and gives an indication that the test device functions as required. The control zone provides a consistent signal that does not vary with the concentration of antibiotic in the sample. The control zone can also be used to inform the user that the liquid composition has flowed through the test device. In that sense, the control zone can be used as a flow control. Furthermore, the control zone can be used for comparison to the detection zone.

'Absorbing region' as used herein refers to the part of the test device, which is in lateral flow contact with the detection region and functions to promote lateral flow through the detection region and is capable of absorbing excess liquid sample. The contact an end-to-end connection, but preferably is an overlap between the detection region and the absorbing region. The overlap may be between 1 and 2 mm. The absorbing region is made of porous material. In a preferred embodiment the absorbing region is at least 1 cm.

'Handling region' as used herein relates to a region of the test device that can be used to hold and manipulate the test device without interfering with the test result. The handling region may be a separate region attached to the solid support, but the handling region can also be a part of the solid support itself. The handling region and absorbing region may also be combined into one region, if desired.

In yet another embodiment of the present invention, the test device comprises a member that covers one or more of the sample receiving region, the detection region and the absorbing region. Said member, which can be made of any material, preferably a clear plastic material, advantageously provides protection for said regions with regard to fingerprints and/or mechanical destruction and/or fumes and the like. One or more regions may be covered with a single member, however also multiple members optionally of different materials may be used.

'Porous material' as used herein refers to any material capable of providing lateral flow. Examples of suitable porous materials are polymeric materials such as polyvinyl or polyester, cotton, glass fiber, nitrocellulose, blends of nitrocellulose with polymeric materials, nylon, paper, rayon and the like.

In an embodiment the test device comprises a detection region that is longer than the absorbing region, an absorbing region that is longer than the handling region, and a handling region that is longer than the sample receiving region.

The test devices according to the present invention are manufactured by the methods known to the skilled in the art. Solid supports can have the form of cards. These can be prepared, for example, using commercially available laminators. The cards can be laminated. Onto the cards the various regions can be attached. The capture reagents used are deposited on the detection region in the form of solutions, before or after the assembly of the cards. These solutions can be deposited very precisely using commercially available apparatus such as dispensers from BioDot, Inc. Before and/or after application of the detection and/or control zone, the detection region can be blocked by for instance spraying a blocking solution. Preferred blocking solutions comprise a buffer e.g. an organic buffer such as a Tris buffer, a surfactant e.g. Tween such as Tween-20, and a protein such as bovine serum albumin. Preferably, the blocking solution is not sprayed directly onto the detection zone and/or control zone. The deposited solutions can be immediately evaporated, for example, by placing the card under a stream of hot air. After all regions and zones have been applied, the cards are preferably dried in a dry atmosphere, i.e. an atmosphere having a relative humidity of <50%, <40%, <30%, <20%, <10%, preferably 0%. For large-scale production it is also possible to prepare rolls. Subsequently, the cards and rolls bearing the desired capture reagents can be cut into strips, each of these strips constituting a test device according to the invention. Alternatively, the capture reagents can also be deposited on the detection region prior to the assembly of the cards or rolls by simply immersing the detection region in a solution containing the capture reagents.

The current invention is also directed to a kit comprising a labeled antibiotic binding protein, a labeled control reagent, and a test device according to the present invention. The test device is preferably stored in a package comprising a desiccant. Preferably, the labeled antibiotic binding protein and labeled control reagent are present in a container, preferably in a single container. Preferably, the kit comprises more than one container and more than one test device, e.g. 10, 20, 30, 40, 50 or even 100 containers and/or test devices. The kit according to the present invention may also comprise a sampling device. This is a device with the aid of which sample, e.g. liquid sample, can be added to the labeled antibiotic binding protein and labeled control reagent. Examples include, but are not limited to, a container (optionally with volume markings), a syringe, a pipette or an automated pipetting system. Such a syringe or pipette may be designed in such a fashion that with only one mode of operation a predetermined volume can be withdrawn from the liquid sample to be analyzed. Optionally, systems known in the art with which more than one syringe or pipette can be operated with one single handling may be applied. In case, the kit comprises a sampling device such as a pipette, it may additionally comprise pipette tips. Preferably, the amount of pipette tips is equal to the amount of containers (i.e. the containers wherein the labeled antibiotic binding protein and labeled control reagent are present) and test devices. This way, with only one pipette different samples can be applied to different containers. In case the kit comprises disposable pipettes as sampling device, the amount of disposable pipettes is equal to the amount of containers (i.e. the containers wherein the labeled antibiotic binding protein and labeled control reagent are present) and test devices.

Optionally, the kit further comprises an insert with instructions for use and/or a means for setting the time needed for incubation. Optionally, the kit further comprises a thermostatic device such as an incubator or a water bath, with the aid of which samples can be kept at a pre-set temperature, such as the temperature at which the liquid sample, the labeled antibiotic binding protein, the labeled control reagent and optionally the test device should be incubated. Preferably, said thermostatic device is designed in such a fashion that it can hold the containers filled with the labeled antibiotic binding protein, the labeled control reagent, the liquid sample and optionally the test device. Optionally, the thermostatic device is coupled to a means for setting the time needed for incubation such that heating is stopped after lapse of a pre-set period. Optionally, the kit also comprises a sample-reading device, a data carrier loaded with a computer program suitable for instructing a computer to analyze digital data obtained from the sample-reading device.

The embodiments and features disclosed above for the method of the present invention also pertain to the test device and kit according to the present invention. The embodiments and features disclosed above for the test device of the present invention also pertain to the method and kit according to the present invention. The embodiments and features disclosed above for the kit of the present invention also pertain to the test device and method according to the present invention.

EXAMPLE 1

Preparation of the Test Device

A nitrocellulose HF90 membrane (Millipore; length 25 mm) was used as a detection region. The membrane was glued to a polystyrene laminated card (thickness 0.254 mm) 8 mm from the proximal end of the card. Next, the detection zone and control zone were applied onto the nitrocellulose membrane. The detection zone was applied by dispensing 1 mg/ml of a 7ACA-spacer-BSA conjugate in 20 mM $KPO_4$-buffer (pH 7.5) with a Biodot Dispense workstation XYZ 3050 with frontline at 0.2 µl/cm. The control zone was applied by dispensing 0.15 mg/ml of an anti-IgY antibody in 20 mM $KPO_4$-buffer (pH 7.5) comprising 0.675 mg/ml BSA, 5% w/v saccharose and 20 mM NaCl with a Biodot Dispense workstation XYZ 3050 with frontline at 0.8 µl/cm. After drying of the zones, the nitrocellulose membrane was blocked by spraying a solution comprising 10 mM Tris buffer (pH 8) comprising 2% w/v BSA and 0.05% w/v Tween-20 using a Biodot Dispense workstation XYZ 3050 with airjet 3x. The solution was sprayed onto the membrane at a distance of 2 mm below the detection zone. Thereafter, the sample receiving region (VF2 membrane from Millipore; length 1 cm) was glued at the proximal end of the card overlapping 2 mm with the nitrocellulose membrane. The absorbing region (10038 membrane from Millipore; length 20 mm) was glued at the distal end of the card with an overlap of 2 mm on the nitrocellulose membrane. The obtained cards were dried at 37° C. in a dry atmosphere (0% relative humidity). The card was cut in strips of 5.2 mm width and kept at a dry atmosphere (0% relative humidity).

EXAMPLE 2

Preparation of the Labeled Antibiotic Binding Protein and Labeled Control Reagent Streptavidin-coated gold particles were synthesized by reacting colloidal gold (diameter 40 nm; 1 OD/ml) with 10 µg/ml streptavidin. Next, the obtained solution was concentrated by tangential flow filtration, washed and stored in a Tris buffer (pH 8) including NaCN. Penicillin binding protein purified from *Bacillus stearothermophilus* was biotinylated (1:4) with D-biotinyl-epsilon-aminocaproic acid-N-hydroxysuccinimide ester. Next, the penicillin binding protein-gold conjugate was synthesized by reacting 1.5 µg biotinylated penicillin binding protein with 1 OD streptavidin-coated gold particles for 1 hour, followed by centrifugation at 10,000×g for 5 minutes and resuspension of the obtained pellet in 45 mM bicarbonate buffer comprising 0.1% w/v Triton X-100 (pH 9.6).

IgY-coated gold particles were synthesized by reacting colloidal gold (diameter 40 nm; 1 OD/ml with 10 µg/ml IgY. Next, the obtained solution was centrifuged at 7,500×g for 10 minutes and the obtained pellet was resuspended in a Tris buffer (pH 8), washed by another round of centrifugation and resuspension of the obtained pellet in a Tris buffer (pH 8) and stored in a Tris-buffer (pH 8) including NaCN.

Thereafter, 140-200 mOD of the penicillin binding protein-gold conjugate and 5-20 mOD of the IgY-gold conjugate was solubilized in 100 µl buffer (80 mM Tris buffer comprising 0.01% w/v Triton-X-100, 0.4% w/v BSA, 5% v/v glycerin and 2% w/v saccharose (pH 8.5)) and 0.75 µl of the solution was dispensed per tube and dried for 12 hours at 40° C. The obtained tubes were sealed.

EXAMPLE 3

Detection of Antibiotics with the Test Device

150 µl of spiked milk was added per tube containing the dried conjugates. The concentration of penicillin G in the added milk varied from 0 to 4 ng/g (tube 1: 0 ng/g; tube 1: 1 ng/g; tube 2: 2 ng/g; tube 3: 3 ng/g; and tube 4: 4 ng/g). The obtained liquid composition was incubated for 2 minutes at 64° C. in an incubator. A test device was put into the tube and incubated for 3 minutes at 64° C. in the incubator. The result was read by eye.

The results are shown in Table 1. The results show that the intensity of the control zone remained stable for any concentration penicillin G in the milk. The signal of the detection zone clearly was less intense when the concentration of penicillin G in the milk was 2 ng/g or higher. At concentrations of 0 ng/g and 1 ng/g the intensity of the detection zone was clearly higher than the intensity of the control zone. At concentrations of 2 ng/g and 3 ng/g the signal intensity of the detection zone was similar to the signal intensity of the control zone. At a concentration of 4 ng/g the intensity of the detection zone was significantly lower than the intensity of the control zone.

EXAMPLE 4

Influence of the Incubation Temperature on the Performance of the Test Device

The test devices were made as described in Example 1 with the proviso that the test devices did not contain a control zone. The labeled antibiotic binding protein was prepared as described in Example 2.

In a first experiment, the labeled antibiotic binding protein was diluted in 200 µL raw milk (25 nM final concentration) and incubated at 64° C. for 5 minutes. In a second experiment the labeled antibiotic binding protein was diluted in 200 µL raw milk (25 nM final concentration) and incubated at 47.5° C. for 5 minutes. After incubation, a test device was introduced vertically in each milk solution and incubation continued for another 10 minutes. After incubation, the signal intensity of the detection zone and the amount of remaining gold in the sample receiving region were evaluated by eye.

There was a significant difference in the amount of remaining labeled binding proteins in the sample receiving region. The sample receiving region with milk incubated at 47.5° C. showed more labeled binding protein than the sample receiving region with milk incubated at 64° C. Ergo, there is a better milk flow at 64° C. than at 47.5° C. There was no significant difference in the intensity of the labeled binding protein at the detection zone.

EXAMPLE 5

Influence of the Length of the Absorbing Region on the Performance of the Test Device Test devices were prepared as described in Example 4. Test devices having an absorbing region of 2 cm length, 2.5 cm length and 5 cm length were prepared. Labeled antibiotic binding protein was prepared as described in Example 2.

Labeled antibiotic binding protein was diluted in 200 µL raw milk (25 nM final concentration) and incubated at 47.5° C. for 5 minutes. Then, a test device having a 2 cm long absorbing region, a 2.5 cm long absorbing region or a 5 cm long absorbing region were vertically introduced into the milk and incubated for 10 minutes at 47.5° C. After incubation, the signal intensity of the detection zone and the amount of remaining gold in the sample receiving region were detected by eye.

The results show that neither the amount of gold remaining in the sample receiving region nor the intensity of the detection zone differed by changing the length of the absorbing region and that the length of the absorbing region can be reduced to 2 cm without loss of intensity at the detection zone.

Additionally, test devices are prepared as described in Example 1. Test devices having an absorbing region of 0.5 cm length, 1 cm of length and 2 cm of length are prepared. Labeled antibiotic binding protein is prepared as described in Example 2.

Labeled antibiotic binding protein is diluted in 150 μL raw milk and incubated at 64° C. for 2 minutes. Then, test devices having a 0.5 cm long absorbing region, a 1 cm long absorbing region or a 2 cm long absorbing region are vertically introduced into the milk and incubated for 3 minutes at 64° C. After incubation, the signal intensity of the detection zone and the amount of remaining gold in the sample receiving region are detected by eye.

The results show that the amount of gold remaining in the sample receiving region is equal between test devices having an absorbing region having a length of 1 cm and test devices having an absorbing region having a length of 2 cm. Moreover, the results show that the intensity of the control and detection zone of test devices having an absorbing region having a length of 1 cm or 2 cm is strong. When the length of the absorbing region of the test device is reduced to 0.5 cm, the signal intensity of the control and detection zone is significantly reduced. The length of the absorbing region of the test device should therefore be at least 1 cm to have a good signal at the control and detection zone.

EXAMPLE 6

Influence of the Membrane Type of the Sample Receiving Region on the Performance of the Test Device Test devices were prepared as described in Example 1. The sample receiving region was made from a membrane with a pore size of 1 μm, a pore size ranging between 3 and 8 μm or a pore size of 50 μm. The labeled antibiotic binding protein and labeled control reagent were prepared as described in Example 2. The test was performed as described in Example 3 with the proviso that the milk was not spiked with antibiotics.

The results show that there is no signal at the control and detection zone when the pore size of the sample receiving region was 1 μm or 50 μm. An intense signal at the control and detection zone was detected when the pore size of the sample receiving region was between 3 and 8 μm. A sample receiving region having a pore size of between 3 and 8 μm is able to remove particles from the milk that negatively influence the outcome of the test. Sample receiving regions having a pore size of 1 μm are clogged by the particles in the milk, while sample receiving regions having a pore size of 50 μm allow the particles in the milk to flow to the detection region and clog the detection region.

EXAMPLE 7

Influence of the Membrane Type of the Sample Receiving Region on the Performance of the Test Device Test devices were prepared as described in Example 1. The sample receiving region was made from a polyvinyl alcohol-bound glass fiber membrane (a VF2 membrane), a glass fiber membrane (a GBF-R4 membrane or a GBF-R7L membrane), a cellulose membrane (an APO45 membrane) or a polyester membrane (a PT-R5 membrane). The labeled antibiotic binding protein and labeled control reagent were prepared as described in Example 2. The test was performed as described in Example 3 with the proviso that the milk was not spiked with antibiotics. After the test was done, the signal intensity of the detection zone was measured by means of absorption measurements at 535 nm by an ESE-Quant Lateral Flow reader (Qiagen).

The results are given in Table 2. They show that the signal intensity of the detection zone was stronger when a polyvinyl alcohol-bound glass fiber membrane (a VF2 membrane) was used compared to when the other membranes were used. The polyvinyl alcohol-bound glass fiber membrane is preferred, as it enables better signal detection at the detection zone.

EXAMPLE 8

Influence of the Membrane Type of the Detection Region on the Performance of the Test Device Test devices were prepared as described in Example 1. The detection region was made from a HF75, HF90 or HF120 membrane. The labeled antibiotic binding protein and labeled control reagent were prepared as described in Example 2. The test was performed as described in Example 3 with the proviso that the milk was not spiked with antibiotics.

The results are given in Table 3. They show that the HF90 membrane is the preferred membrane for the detection region of the test device, as the detection zone on a HF90 membrane gives a stronger signal intensity than the detection zone on a HF75 or a HF120 membrane.

EXAMPLE 9

Influence of the Concentration of the Immobilized Antibiotic on the Performance of the Test Device Test devices were prepared as described in Example 1 with the proviso that the concentration of antibiotic (7ACA-spacer-BSA conjugate) spotted onto the detection zone was varied. The concentration of antibiotic was calculated as the amount of antibiotic (in mg) per unit of length (in mm) of the detection zone. The labeled antibiotic binding protein and labeled control reagent were prepared as described in Example 2. The test was performed as described in Example 3 with the proviso that the milk was not spiked with antibiotics. The signal intensity and the shape of the detection zone were analyzed.

The results are given in Table 4. They demonstrate that the signal at the detection zone is difficult to detect, when the test device comprises 0.1 mg/mm or 4 mg/mm antibiotic immobilized at the detection zone. The former gives a sharp line but has a low signal intensity, while the latter has a strong signal intensity but gives a diffuse line (i.e. signal is fading out in the direction of the milk flow), making the signal hard to detect. In contrast, when the test device comprises 2 mg/mm antibiotic immobilized at the detection zone, the line is sharp and the signal intensity is strong. This results in a very good detectability of the signal at the detection zone.

EXAMPLE 10

Influence of the Type of Buffer of the Immobilized Antibiotic on the Performance of the Test Device Test devices were prepared as described in Example 1 with the proviso that the antibiotic spotted onto the detection zone was present in a 20 mM $KPO_4$ buffer (pH 7.5) or in a 10 mM Tris buffer (pH 8.0). Next, the test devices were stored at 37° C. for two weeks. The labeled antibiotic binding protein and labeled control reagent were prepared as described in Example 2. After storage of the test devices, the test was performed as described in Example 3 with the proviso that milk was not spiked with antibiotics. The signal intensity of the detection zone before and after storage was analyzed.

The results show that the signal intensity of the detection zone decreases after storage for two weeks at 37° C. (compared to before storage) for test devices wherein the antibiotic spotted onto the detection zone was present in a phosphate buffer. The signal intensity of the detection zone stays constant after storage for two weeks at 37° C. (compared to before storage) for test devices wherein the antibiotic spotted onto the detection zone was present in a Tris buffer. From this was concluded that the antibiotic spotted onto the detection zone should preferably be present in an organic buffer such as a Tris buffer and not in an inorganic buffer such as a phosphate such as a $KPO_4$ buffer.

EXAMPLE 11

Influence of the Type of Blocking Solution of the Detection Region on the Performance of the Test Device Test devices were prepared as described in Example 1 with the proviso that after drying of the zones, the nitrocellulose membrane was blocked by spraying with:
 a) no blocking,
 b) a solution comprising 2% w/v BSA, 0.05% w/v Tween-20 in 10 mM Tris (pH 8), or
 c) a solution comprising 2% w/v BSA, 0.05% w/v Tween-20 in 2 mM $KPO_4$ buffer (pH 7.5), Next, the test devices were either used directly in the test (to analyze signal intensity before storage) or the test devices were stored at 37° C. for two weeks (to analyze signal intensity after storage) and then used in the test. The labeled antibiotic binding protein and labeled control reagent were prepared as described in Example 2. The test was performed as described in Example 3 with the proviso that the milk was not spiked with antibiotics. The signal intensity of the detection zone before and after storage was analyzed.

The results show that the signal intensity of the detection zone of test devices blocked with solution b and c was similar before storage, while non-blocked test devices showed a lower signal intensity. The signal intensity of the detection zone of test devices blocked with solution c became weaker when test devices were used that were stored at 37° C. The signal intensity of the detection zone of test devices blocked with solution b was similar before and after storage of the test devices at 37° C. Blocking with an organic buffer such as Tris gives a stable intensity of the detection zone over a long period of time. Blocking with organic buffer such as Tris thus provides test devices having a prolonged shelf-life.

EXAMPLE 12

Influence of the Position of the Application of the Blocking Solution on the Performance of the Test Device Test devices were either prepared as described in Example 1 or prepared as described in Example 1 with the proviso that the blocking solution applied to the nitrocellulose membrane after drying was sprayed directly on the detection zone. The labeled antibiotic binding protein and labeled control reagent were prepared as described in Example 2. The test was performed as described in Example 3 with the proviso that the milk was not spiked with antibiotics.

The results show that the signal intensity of the detection and control zone was less intense (41% and 52%, respectively), when the blocking solution was sprayed directly onto the detection zone compared to when the blocking solution was not sprayed directly onto the detection zone. It can be concluded that the blocking solution should not be sprayed directly onto the detection zone for optimal signal intensity of the detection zone.

EXAMPLE 13

Influence of the Type of Solution used to Apply to the Control Zone on the Performance of the Test Device Test devices were prepared as described in Example 1 with the proviso that the solution used to apply to the control zone comprised:
 a) 0.15 mg/ml anti-IgY antibody, 20 mM $KPO_4$-buffer (pH 7.5)
 b) 0.15 mg/ml anti-IgY antibody, 0.6 mg/ml BSA, 5.0% w/v sucrose, 20 mM NaCl, 20 mM $KPO_4$-buffer (pH 7.5)
 c) 0.075 mg/ml anti-IgY antibody, 0.6 mg/ml BSA, 5.0% w/v sucrose, 20 mM0 NaCl, 20 mM $KPO_4$-buffer (pH 7.5)
 d) 0.04 mg/ml anti-IgY antibody, 0.7 mg/ml BSA, 5.0% w/v sucrose, 20 mM NaCl, 20 mM $KPO_4$-buffer (pH 7.5).

The labeled antibiotic binding protein and labeled control reagent were prepared as described in Example 2. The test was performed as described in Example 3 with the proviso that the milk was not spiked with antibiotics. The signal intensity of the control zone were analyzed.

The results are shown in Table 5. They demonstrate that the signal at the control zone is good to detect, when the solution used to apply the control zone comprises a IgY in combination with at least one additional protein such as BSA, at least one sugar (preferably a disaccharide such as saccharose), and at least one salt such as NaCl.

In addition, it was investigated if the speed of dispensing the control zone onto the detection region was of importance on the performance of the test device. The results show that when dispensing the control zone at a speed of 0.2 μl/cm or a speed of 0.8 μl/cm the obtained control zone was too thin and not detectable. When the control zone was dispensed at a speed of 1.5 μl/cm, the detectability of the control zone was good.

EXAMPLE 14

Influence of the Humidity During Drying of the Cards on the Performance of the Test Device Test devices were either prepared as described in Example 1 or prepared as described in Example 1 with the proviso that the obtained cards were dried at 37° C. in a semi-dry atmosphere (about 50% relative humidity). After preparation, the test devices were stored at 37° C. for two weeks. The labeled antibiotic binding protein and labeled control reagent were prepared as described in Example 2. The test was performed as described in Example 3 with the proviso that the milk was not spiked with antibiotics.

The results show that the signal intensity of the detection zone is less intense when the obtained cards were dried at 37° C. in a semi-dry atmosphere (about 50% relative humidity) than when the obtained cards were dried at 37° C. in a dry atmosphere (0% relative humidity). This demonstrates that the shelf-life of the test devices is better when the test devices are dried at very low relative humidity than when the test devices are dried at high relative humidity.

EXAMPLE 15

Influence of the Presence of Desiccant to Packaged Test Devices on the Performance of the Test Device Test devices are prepared as described in Example 1 and divided into two parts. The first part is stored for 1 year at 4° C. in a closed packaging without desiccant, while the second part is stored for 1 year at 4° C. in the closed packaging with desiccant. After storage, the test devices are used in the test. The labeled antibiotic binding protein and labeled control reagent are prepared as described in Example 2. The test is performed as described in Example 3 with the proviso that the milk is not spiked with antibiotics.

The results show that the signal intensity of the detection zone is stronger for test devices stored in a packaging with desiccant than for test devices stored in a packaging without desiccant.

EXAMPLE 16

Influence of the Type of Solubilization Buffer on the Performance of the Test Device The labeled antibiotic binding protein and labeled control reagent were either prepared as described in Example 2 or prepared as described in Example 2 with the proviso that a 70 mM MOPS buffer instead of a 100 mM Tris buffer was used as solubilization buffer. All buffers used comprised 0.0025% w/v Triton-X-100, 0.4% w/v BSA, 5% v/v glycerin and 2% w/v saccharose and had a pH of 8.5 and 0.75 µl of the solution was dispensed per tube and dried for 12 hours at 40° C. The obtained tubes were sealed. Test devices were prepared as described in Example 1 and the test was performed as described in Example 3 with the proviso that the milk was not spiked with antibiotics.

The results are given in Table 6. They demonstrate that the signal intensity of the detection zone is stronger when the labeled antibiotic binding protein and the labeled control reagent are solubilized in a Tris buffer than when they are solubilized in a MOPS buffer. From this can be concluded that include organic buffers such as Tris buffers instead of inorganic buffers e.g. phosphate containing buffers such as MOPS buffers should be included in the containers (i.e. test tubes) comprising the labeled antibiotic binding protein and the labeled control reagent.

EXAMPLE 17

Influence of the Triton X-100 Concentration of the Solubilization Buffer on the Performance of the Test Device The labeled antibiotic binding protein and labeled control reagent were prepared as described in Example 2 with the proviso that buffers with different concentrations of Triton X-100 were used. All buffers used comprised 80 mM Tris, 0.4% w/v BSA, 5% v/v glycerin, 2% w/v saccharose and had a pH of 8.5 and 0.75 µl of the solution was dispensed per tube and dried for 12 hours at 40° C. The obtained tubes were sealed. Test devices were prepared as described in Example 1 and the test was performed as described in Example 3 with the proviso that the milk was not spiked with antibiotics.

The results are given in Table 7. They demonstrate that the signal intensity of the detection zone is absent in absence of Triton X-100. It can be concluded from this experiment that the Triton X-100 concentration in the solubilization buffer should be above 0. From this example can further be concluded that a surfactant e.g. a nonionic surfactant such as Triton X-100 should be included in the containers (i.e. test tubes) comprising the labeled antibiotic binding protein and the labeled control reagent. Preferably, Triton X-100 should be included in a concentration of above 0.0025% w/v, e.g. about 0.01% w/v, in the containers (i.e. test tubes) comprising the labeled antibiotic binding protein and the labeled control reagent.

EXAMPLE 18

Influence of the BSA Concentration of the Solubilization Buffer on the Performance of the Test Device The labeled antibiotic binding protein and labeled control reagent were prepared as described in Example 2 with the proviso that buffers with different amounts of BSA were used. All buffers used comprised 80 mM Tris, 0.01% w/v Triton X-100, 5% v/v glycerin, 2% w/v saccharose and had a pH of 8.5 and 0.75 µl of the solution was dispensed per tube and dried for 12 hours at 40° C. The obtained tubes were sealed. Test devices were prepared as described in Example 1 and the test was performed as described in Example 3 with the proviso that the milk was not spiked with antibiotics.

The results are given in Table 8. They demonstrate that the signal intensity of the detection zone is medium when buffers with low amounts of BSA, e.g. 0.2% w/v, were used. When buffers with higher amounts of BSA, e.g. 0.4% or 0.8% w/v, were used, the signal intensity was stronger. From this can be concluded that a protein e.g. an albumin such bovine serum albumin (BSA) should be included in amounts of above 0.2% w/v in the containers (i.e. test tubes) comprising the labeled antibiotic binding protein and the labeled control reagent.

EXAMPLE 19

Influence of the Glycerin Concentration of the Solubilization Buffer on the Performance of the Test Device The labeled antibiotic binding protein and labeled control reagent were prepared as described in Example 2 with the proviso that buffers with different amounts of glycerin were used. All buffers used comprised 80 mM Tris, 0.01% w/v Triton X-100, 0.4% w/v BSA, 2% w/v saccharose and had a pH of 8.5 and 0.75 µl of the solution was dispensed per tube and dried for 12 hours at 40° C. The obtained tubes were sealed. Test devices were prepared as described in Example 1 and the test was performed as described in Example 3 with the proviso that the milk was not spiked with antibiotics.

The results are given in Table 9. They demonstrate that the signal intensity of the detection zone is weak in the absence of glycerin, while in the presence of glycerin the signal intensity is medium to strong. The results further show that the optimal glycerin concentration is 5% v/v. From this example can be concluded that a polyol such as glycerin should be included in the containers (i.e. test tubes) comprising the labeled antibiotic binding protein and the labeled control reagent. Preferably, the amount of glycerin is about 5% v/v.

EXAMPLE 20

Influence of the Saccharose Concentration of the Solubilization Buffer on the Performance of the Test Device The labeled antibiotic binding protein and labeled control reagent were prepared as described in Example 2 with the proviso that buffers with different amounts of saccharose were used. All buffers used comprised 80 mM Tris, 0.01% w/v Triton X-100, 0.4% w/v BSA, 5% v/v glycerin and had a pH of 8.5 and 0.75 µl of the solution was dispensed per tube and dried for 12 hours at 40° C. The obtained tubes were sealed. Test devices were prepared as described in Example 1 and the test was performed as described in Example 3 with the proviso that the milk was not spiked with antibiotics.

The results are given in Table 10. They demonstrate that the signal intensity of the detection zone is weak when low amounts of saccharose are used. The results further show that the optimal saccharose concentration is 2% w/v. From this example can be concluded that a sugar e.g. a disaccharide such as saccharose should be included in the containers (i.e. test tubes) comprising the labeled antibiotic binding protein and the labeled control reagent. Preferably, the amount of saccharose is about 2% w/v.

EXAMPLE 21

Influence of the Type of Drying of the Solubilization Buffer on the Performance of the Test Device The labeled antibiotic binding protein and labeled control reagent were prepared as described in Example 2 with the first proviso that the solubilization buffer in the tubes was either dried for 24 hours at 40° C. or was frozen in liquid nitrogen (−80° C.) for 1 hour and then dried under vacuum (0.42 mbar) at a temperature of 10° C. for 20 hours and the second proviso that buffers with different amounts of saccharose were used. The obtained tubes were sealed. Test devices were prepared as described in Example 1 and the test was performed as described in Example 3 with the proviso that the milk was not spiked with antibiotics. After the test was done, the signal intensity of the detection zone was measured by means of absorption measurements at 535 nm by an ESE-Quant Lateral Flow reader (Qiagen).

The results are shown in Table 11. They show that the signal intensity of the detection zone is identical for solubilization buffers dried for 12 hours at 40° C. and solubilization buffers that are lyophilized, when the solubilization buffers comprise 2% w/v saccharose. At saccharose concentrations higher than 2% w/v, lyophilisation gives higher signal intensities, while at saccharose concentrations lower than 2% w/v air drying gives higher signal intensities.

EXAMPLE 22

Influence of the Concentration of Labeled Protein on the Performance of the Test Device Test devices were prepared as described in Example 1 and the labeled antibiotic binding protein and labeled control reagent were prepared as described in Example 2. In this example the influence of the concentration of labeled antibiotic binding protein in milk was evaluated. The labeled antibiotic binding protein was diluted in 150 µl raw milk to a final concentration of 25 nM, 50 nM or 100 nM and incubated at 64° C. for 2 minutes. Then, a test device was vertically introduced in each of the milk solutions and incubated for 3 minutes at 64° C. After incubation, the signal intensity of the detection zone and the amount of remaining gold in the sample receiving region were detected visually.

The results show a significant increase in the signal intensity of the detection zone with increasing concentration of the antibiotic binding protein in the milk. The remaining labeled antibiotic binding protein in the sample receiving region also increases with increase of concentration.

EXAMPLE 23

Sensitivity of the Test Device for Different Antibiotics

The test was done essentially as described in Example 3, with the proviso that different antibiotics at different concentrations were tested.

The results are shown in Table 12. The results demonstrate that different beta-lactam antibiotics can be detected with the test device of the present invention.

EXAMPLE 24

Detection of Antibiotics with the Test Device in Different Products

The test was done essentially as described in Example 3. Instead of raw milk, different dairy matrices were tested. All liquid matrices were measured as such and all powders were first dispersed in water. For milk powder 20 g was dispersed in 250 g distilled water and for whey powder 7.1 g was dispersed in 100 g distilled water.

The results are shown in Table 13. The results show that the test device can be used to detect antibiotics in different dairy matrices with the exception of whey at pH 4.5

EXAMPLE 25

Shelf-Life of the Test Device

The test devices were produced as described above in Examples 1 and 2 and stored at 4° C. At different time periods after production, the test device was used to measure penicillin G. The test was done essentially as described in Example 3.

The results are shown in Table 14. The results show that storage up to about 9 months at 4° C. does not influence the performance of the test devices. The test devices according to the present invention have a shelf-life of at least 9 months.

EXAMPLE 26

Influence of Storage Temperature on Shelf-Life of Test Device

The test devices were produced as described above in Examples 1 and 2 and stored at different temperatures (−20° C. and 30° C.). At different time periods after production, the test device was used to detect penicillin G. The test was done essentially as described in Example 3.

The results are shown in Table 15. The results show that there is no influence on performance of the test device after storage at −20° C. for up to 28 days. In addition, there is no influence on performance of the test device after storage at 30° C. for up to 7 days. After 28 days of storage at 30° C., a small decrease in signal intensity of the detection zone is observed.

EXAMPLE 27

Influence of Milk Composition on the Test Device

Different milk samples from single farmers from Belgium were collected and declared antibiotic-free. The pH, somatic cell count and fat and protein content were analyzed using a Fossomatic 5000 apparatus (Foss, Denmark). Each sample was divided into three subsets. Each subset was then spiked with 0, 3 or 4 ng/g penicillin G. Thereafter, the test was done essentially as described in Example 3.

The results (data not shown) show that the milk composition (milk samples varied in pH from 6.57 to 7.15; in cell count from 20,000 to 6,993,000; in fat content from 0.26% (w/w) to 8.32% (w/w); and in protein content from 3.11% (w/w) to 4.53% (w/w)) does not influence the performance of the test device. None of the samples with 0 ng/g penicillin G was found positive.

EXAMPLE 28

Influence of a Shaking Step on the Test Device

The test was done essentially as described in Example 3, with the proviso that different shaking steps were applied. The shaking steps that were done according to the following methods:

Method a) no shaking steps,
Method b) one shaking step (10 seconds) done after addition of the milk to the labeled antibiotic binding protein and subsequent incubation of the obtained liquid composition, but before contacting the test device with the obtained liquid composition,
Method c) one shaking step (10 seconds) done after addition of the milk to the labeled antibiotic binding protein, but before subsequent incubation of the obtained liquid composition,
Method d) a first shaking step (5 seconds) done after addition of the milk to the labeled antibiotic binding protein, but before subsequent incubation of the obtained liquid composition, and a second shaking step (10 seconds) done after subsequent incubation of the obtained liquid composition, but before contacting the test device with the obtained liquid composition,
Method e) a first shaking step (10 seconds) done after addition of the milk to the labeled antibiotic binding protein, but before subsequent incubation of the obtained liquid composition, and a second shaking step (10 seconds) done after subsequent incubation of the obtained liquid composition, but before contacting the test device with the obtained liquid composition.

The results are shown in Table 16. The results show that absence of shaking negatively influences the signal intensity of the control and the detection zone. In addition, the results show that there is no difference when performing one or two shaking steps. One as well as two shaking steps result in a high signal intensity of the control and the detection zone.

EXAMPLE 29

Influence of Temperature on the Test

The test was done essentially as described in Example 3, with the proviso that the test was done at different temperatures (4° C., 20° C. or 31.5° C.).

The results are shown in Table 17. The results show that the temperature at which the test is done does not influence the intensities of the detection and control zones.

EXAMPLE 30

Influence of Initial Milk Temperature on the Test

The test was done essentially as described in Example 3, with the proviso that the test was done with milk having an initial different temperature (0° C., 4° C., 20° C. or 45° C.). The milk was allowed to reach room temperature shortly before the test was done.

The results are shown in Table 18. The results show that the initial milk temperature does not influence the intensities of the detection and control zones.

TABLE 1

Detection of antibiotics with the test device according to the invention.

| Concentration Penicillin G (ng/g) | 0 | 1 | 2 | 3 | 4 |
|---|---|---|---|---|---|
| Intensity of the control zone* | 2 | 2 | 2 | 2 | 2 |
| Intensity of the detection zone* | 3 | 3 | 2 | 2 | 1 |

*0: no intensity; 1: low intensity; 2: medium intensity; 3: high intensity.

TABLE 2

Signal intensity of the detection zone for different sample receiving region membranes measured by means of absorption.

| Type of membrane of sample receiving region | Signal intensity (measured by absorption at 535 nm) |
|---|---|
| VF2 | 683 |
| GFB-R4 | 472 |
| GFB-R7L | 325 |
| PT-R5 | 629 |
| AP045 | 370 |

TABLE 3

Signal intensity of the detection zone and total test time for different detection region membrane types.

| Membrane type | Signal intensity* | Total test time (minutes) |
|---|---|---|
| HF 75 | 1 | 4 |
| HF 90 | 4 | 5 |
| HF 120 | 0 | >20 |

*0: not visible; 1: very weak signal; 2: weak signal; 3: medium signal; 4: strong signal; 5: very strong signal

TABLE 4

Signal intensity and shape of the detection zone for different concentrations of antibiotic immobilized at the detection zone.

| Concentration antibiotic (mg/mm) | Signal intensity of the front of the detection zone[1] | Shape of detection zone | Detectability of signal of detection zone[2] |
|---|---|---|---|
| 0.1 | 1 | Sharp line | 2 |
| 2 | 4 | Sharp line | 5 |
| 4 | 5 | Diffuse line | 3 |

[1]0: not visible; 1: very weak signal; 2: weak signal; 3: medium signal; 4: strong signal; 5: very strong signal
[2]0: not detectable; 1: very bad; 2: bad; 3: medium; 4: good; 5: very good

TABLE 5

Signal intensity and shape of the control zone for different solution applied to the control zone.

| Solution | Detectability of signal of control zone[1] |
|---|---|
| a | 1 |
| b | 3 |
| c | 4 |
| d | 3 |

[1]0: not detectable; 1: very bad; 2: bad; 3: medium; 4: good; 5: very good

TABLE 6

Signal intensity of the detection zone for different solubilization buffers.

| Buffer type | Signal intensity* |
|---|---|
| Tris/HCl | 4 |
| MOPS | 3 |

*0: not visible; 1: very weak signal; 2: weak signal; 3: medium signal; 4: strong signal; 5: very strong signal

TABLE 7

Signal intensity of the detection zone for buffers with different Triton X-100 concentrations.

| Triton X-100 concentration (w/v) | Signal intensity* |
|---|---|
| 0 | 0 |
| 0.0025 | 3 |
| 0.01 | 4 |

*0: not visible; 1: very weak signal; 2: weak signal; 3: medium signal; 4: strong signal; 5: very strong signal

TABLE 8

Signal intensity of the detection zone for buffers with different BSA concentrations.

| BSA concentration (w/v) | Signal intensity* |
|---|---|
| 0.2 | 3 |
| 0.4 | 5 |
| 0.8 | 4 |

*0: not visible; 1: very weak signal; 2: weak signal; 3: medium signal; 4: strong signal; 5: very strong signal

TABLE 9

Signal intensity of the detection zone for buffers with different glycerin concentrations.

| glycerin concentration (v/v) | Signal intensity* |
|---|---|
| 0 | 2 |
| 3 | 3 |
| 5 | 4 |
| 7 | 3 |
| 10 | 3 |

*0: not visible; 1: very weak signal; 2 weak signal; 3: medium signal; 4: strong signal; 5: very strong signal

TABLE 10

Signal intensity of the detection zone for buffers with different saccharose concentrations.

| saccharose concentration (w/v) | Signal intensity* |
|---|---|
| 0.1 | 2 |
| 0.2 | 2 |
| 0.5 | 2 |
| 1 | 2 |
| 2 | 4 |
| 4 | 2 |

*0: not visible; 1: very weak signal; 2 weak signal; 3: medium signal; 4: strong signal; 5: very strong signal

TABLE 11

Signal intensity of the detection zone for different drying methods at different saccharose concentrations measured by means of absorption.

| Saccharose concentration (% w/v) | Air drying Signal intensity (measured by absorption at 535 nm) | Lyophilization |
|---|---|---|
| 0.5 | 0.160 | 0.116 |
| 1 | 0.149 | 0.128 |
| 2 | 0.156 | 0.157 |
| 4 | 0.149 | 0.160 |
| 8 | 0.065 | 0.157 |

TABLE 12

Detection of several antibiotics with the test device according to the invention.

| Antibiotic | | | | | | | |
|---|---|---|---|---|---|---|---|
| Amoxicillin | Concentration (ng/g) | 0.0 | 3.3 | 4.3 | 5.3 | 6.3 | 7.3 |
| | Intensity of detection zone | 3 | 2 | 1 | 1 | 0 | 0 |
| | Intensity of control zone | 2 | 2 | 2 | 2 | 2 | 2 |
| Ampicillin | Concentration (ng/g) | 0.0 | 5.3 | 6.9 | 8.5 | 10.1 | 11.7 |
| | Intensity of detection zone | 3 | 2 | 1 | 0 | 0 | 0 |
| | Intensity of control zone | 2 | 2 | 2 | 2 | 2 | 2 |
| Cefalonium | Concentration (ng/g) | 0.0 | 3.2 | 4.0 | 4.8 | 5.6 | 6.4 |
| | Intensity of detection zone | 3 | 2 | 1 | 0 | 0 | 0 |
| | Intensity of control zone | 2 | 2 | 2 | 2 | 2 | 2 |
| Cefquinome | Concentration (ng/g) | 0.0 | 12.5 | 15.8 | 19.1 | 22.4 | 25.7 |
| | Intensity of detection zone | 3 | 2 | 1 | 0 | 0 | 0 |
| | Intensity of control zone | 2 | 2 | 2 | 2 | 2 | 2 |
| Ceftiofur | Concentration (ng/g) | 0.0 | 4.0 | 5.1 | 6.2 | 7.3 | 8.4 |
| | Intensity of detection zone | 3 | 2 | 1 | 0 | 0 | 0 |
| | Intensity of control zone | 2 | 2 | 2 | 2 | 2 | 2 |
| Cloxacillin | Concentration (ng/g) | 0.0 | 32.5 | 43.2 | 53.9 | 64.6 | 75.3 |
| | Intensity of detection zone | 3 | 1 | 0 | 0 | 0 | 0 |
| | Intensity of control zone | 2 | 2 | 2 | 2 | 2 | 2 |
| Cefalexin | Concentration (ng/g) | 0.0 | 34.0 | 43.0 | 52.0 | 61.0 | 70.0 |
| | Intensity of detection zone | 3 | 2 | 1 | 0 | 0 | 0 |
| | Intensity of control zone | 2 | 2 | 2 | 2 | 2 | 2 |
| Cefazolin | Concentration (ng/g) | 0.0 | 10.0 | 12.5 | 15.0 | 17.5 | 20.0 |
| | Intensity of detection zone | 3 | 2 | 1 | 0 | 0 | 0 |
| | Intensity of control zone | 2 | 2 | 2 | 2 | 2 | 2 |
| Cefoperazone | Concentration (ng/g) | 0.0 | 4.0 | 4.9 | 5.8 | 6.7 | 7.6 |
| | Intensity of detection zone | 3 | 2 | 2 | 1 | 1 | 0 |
| | Intensity of control zone | 2 | 2 | 2 | 2 | 2 | 2 |

TABLE 12-continued

Detection of several antibiotics with the test device according to the invention.

| Antibiotic | | | | | | | |
|---|---|---|---|---|---|---|---|
| Dicloxacillin | Concentration (ng/g) | 0.0 | 15.0 | 20.0 | 25.0 | 30.0 | 35.0 |
| | Intensity of detection zone | 3 | 3 | 2 | 2 | 1 | 0 |
| | Intensity of control zone | 2 | 2 | 2 | 2 | 2 | 2 |
| Nafcillin | Concentration (ng/g) | 0.0 | 40.0 | 50.5 | 61.0 | 71.5 | 82.0 |
| | Intensity of detection zone | 3 | 3 | 2 | 1 | 0 | 0 |
| | Intensity of control zone | 2 | 2 | 2 | 2 | 2 | 2 |
| Oxacillin | Concentration (ng/g) | 0.0 | 27.0 | 34.8 | 42.6 | 50.4 | 58.2 |
| | Intensity of detection zone | 3 | 2 | 2 | 1 | 0 | 0 |
| | Intensity of control zone | 2 | 2 | 2 | 2 | 2 | 2 |

*0: no intensity; 1: low intensity; 2: medium intensity; 3: high intensity.

TABLE 13

Detection of Penicillin G with the test device according to the invention in different dairy matrices.

| | Intensity of detection zone | | | Intensity of control zone | | |
|---|---|---|---|---|---|---|
| | Concentration Pen G (ppb) | | | | | |
| Matrix | 0 | 3 | 4 | 0 | 3 | 4 |
| Frozen raw milk | 3 | 2 | 1 | 2 | 2 | 2 |
| Milk powder | 3 | 2 | 1 | 2 | 2 | 2 |
| Low fat processed milk | 3 | 2 | 1 | 2 | 2 | 2 |
| Pasteurized milk | 3 | 2 | 1 | 2 | 2 | 2 |
| UHT milk | 3 | 2 | 1 | 2 | 2 | 2 |
| Low fat UHT milk | 3 | 2 | 1 | 2 | 2 | 2 |
| Frozen raw goat milk | 1 | 1 | 0 | 2 | 2 | 2 |
| Frozen raw buffalo milk | 1 | 1 | 0 | 2 | 2 | 2 |
| Frozen raw sheep milk | 1 | 1 | 0 | 2 | 2 | 2 |
| Whey pH 4.5 | 0 | 0 | 0 | 0 | 0 | 0 |
| Whey powder | 3 | 2 | 1 | 2 | 2 | 2 |
| Cream 10% | 3 | 2 | 1 | 2 | 2 | 2 |
| Cocoa | 3 | 2 | 1 | 2 | 2 | 2 |
| Cream 40% | 3 | 2 | 2 | 2 | 2 | 2 |

*0: no intensity; 1: low intensity; 2: medium intensity; 3: high intensity.

TABLE 14

Detection of Penicillin G with the test device according to the invention after storage of the test device at 4° C.

| | Intensity of detection zone | | | Intensity of control zone | | |
|---|---|---|---|---|---|---|
| | Concentration Pen G (ppb) | | | | | |
| Storage time (weeks) | 0 | 3 | 4 | 0 | 3 | 4 |
| 0 | 3 | 2 | 1 | 2 | 2 | 2 |
| 4 | 3 | 2 | 1 | 2 | 2 | 2 |
| 7 | 3 | 2 | 1 | 2 | 2 | 2 |
| 15 | 3 | 2 | 1 | 2 | 2 | 2 |
| 18 | 3 | 2 | 1 | 2 | 2 | 2 |
| 26 | 3 | 2 | 1 | 2 | 2 | 2 |

*0: no intensity; 1: low intensity; 2: medium intensity; 3: high intensity.

TABLE 15

Detection of Penicillin G with the test device according to the invention after storage of the test device at −20° C. or 30° C.

| | Intensity of detection zone | | | Intensity of control zone | | |
|---|---|---|---|---|---|---|
| | Concentration Pen G (ppb) | | | | | |
| Storage time (days) | 0 | 3 | 4 | 0 | 3 | 4 |
| Storage temperature −20° C. | | | | | | |
| 0 | 3 | 2 | 1 | 2 | 2 | 2 |
| 3 | 3 | 2 | 1 | 2 | 2 | 2 |
| 7 | 3 | 2 | 1 | 2 | 2 | 2 |
| 28 | 3 | 2 | 1 | 2 | 2 | 2 |
| Storage temperature 30° C. | | | | | | |
| 0 | 3 | 2 | 1 | 2 | 2 | 2 |
| 3 | 3 | 2 | 1 | 2 | 2 | 2 |
| 7 | 3 | 2 | 1 | 2 | 2 | 2 |
| 28 | 3 | 1 | 0 | 2 | 2 | 2 |

*0: no intensity; 1: low intensity; 2: medium intensity; 3: high intensity.

TABLE 16

Detection of Penicillin G with the test device according to the invention after different shaking steps.

| | Intensity of detection zone | | | Intensity of control zone | | |
|---|---|---|---|---|---|---|
| | Concentration Pen G (ppb) | | | | | |
| | 0 | 3 | 4 | 0 | 3 | 4 |
| Method a | 2 | 1 | 1 | 1 | 1 | 1 |
| Method b | 3 | 2 | 1 | 2 | 2 | 2 |
| Method c | 3 | 2 | 1 | 2 | 2 | 2 |
| Method d | 3 | 2 | 1 | 2 | 2 | 2 |
| Method e | 3 | 2 | 1 | 2 | 2 | 2 |

*0: no intensity; 1: low intensity; 2: medium intensity; 3: high intensity.

TABLE 17

Detection of Penicillin G with the test device according to the invention at different temperatures.

| | Intensity of detection zone | | | Intensity of control zone | | |
|---|---|---|---|---|---|---|
| | Concentration Pen G (ppb) | | | | | |
| Temperature (° C.) | 0 | 3 | 4 | 0 | 3 | 4 |
| 4 | 3 | 2 | 1 | 2 | 2 | 2 |
| 20 | 3 | 2 | 1 | 2 | 2 | 2 |
| 31.5 | 3 | 2 | 1 | 2 | 2 | 2 |

*0: no intensity; 1: low intensity; 2: medium intensity; 3: high intensity.

TABLE 18

Detection of Penicillin G with the test device according to the invention with milk having a different initial temperature.

| Initial milk temperature (° C.) | Intensity of detection zone | | | Intensity of control zone | | |
|---|---|---|---|---|---|---|
| | Concentration Pen G (ppb) | | | | | |
| | 0 | 3 | 4 | 0 | 3 | 4 |
| 0 | 3 | 2 | 1 | 2 | 2 | 2 |
| 4 | 3 | 2 | 1 | 2 | 2 | 2 |
| 20 | 3 | 2 | 1 | 2 | 2 | 2 |
| 45 | 3 | 2 | 1 | 2 | 2 | 2 |

*0: no intensity; 1: low intensity; 2: medium intensity; 3: high intensity.

The invention claimed is:

1. A method for detecting a beta-lactam antibiotic in a sample, said method comprising:
   a) contacting a liquid sample with a labeled antibiotic binding protein obtained from an antibiotic-sensitive *Bacillus stearothermophilus* and a labeled control reagent, wherein the labeled antibiotic binding protein and the labeled control reagent are present in a container, to form a liquid composition in the container,
   b) providing a test device having a proximal and a distal end, said test device configured to allow lateral flow from the proximal to the distal end, said test device comprising a solid support comprising the following regions in sequence from the proximal to the distal end:
      i. a sample receiving region,
      ii. a detection region, said detection region comprising at least two zones:
         A. a detection zone comprising an immobilized antibiotic capable of binding the labeled antibiotic binding protein, when said labeled antibiotic binding protein is unbound by antibiotic from the sample, and
         B. a control zone comprising an immobilized binding agent capable of binding the labeled control reagent,
      iii. an absorbing region, and
      iv. optionally, a handling region,
   c) contacting the liquid composition of part a) with the sample receiving region of the test device of part b),
   d) allowing the liquid composition to move from the sample receiving region through the detection region to the absorbing region, so as to allow the liquid composition comprising the labeled antibiotic binding protein and the labeled control reagent to contact the detection zone and the control zone,
   e) detecting a signal at the detection zone and a signal at the control zone, wherein
      i. an absence of antibiotic in the sample is indicated by a presence of a signal at the detection zone that is more intense than the signal at the control zone, and
      ii. a presence of antibiotic in the sample is indicated by an absence of a signal at the detection zone or a presence of a signal at the detection zone that is less intense than the signal at the control zone.

2. A method according to claim 1, wherein the liquid composition is incubated for 30 seconds to 5 minutes before being contacted with the test device.

3. A method according to claim 1, wherein the liquid composition is incubated at 40 to 70° C. before being contacted with the test device.

4. A method according to claim 1, wherein the labeled antibiotic binding protein and the labeled control reagent are present in powder form before being contacted with the liquid sample.

5. A method according to claim 1, wherein the label of the antibiotic binding protein and the control reagent are identical.

6. A method according to claim 1, wherein the antibiotic binding protein and the control reagent are labeled with a gold particle.

7. A method according to claim 1, wherein the control reagent is unable to bind to the antibiotic in the sample.

8. A method according to claim 1, wherein the test device is a test strip.

9. A method according claim 1, wherein the immobilized antibiotic is bound to the solid support by a spacer-protein conjugate.

10. A method according to claim 1, wherein the test device is contacted with the liquid composition for 1 to 5 minutes at a temperature of 40 to 70° C.

11. A method according claim 1, wherein the sample is milk.

12. The method of claim 1, wherein the beta-lactam antibiotic is a cephalosporin.

13. A kit comprising:
   a) a container comprising a labeled antibiotic binding protein from an antibiotic-sensitive *Bacillus stearothermophilus* and a labeled control reagent, and
   b) a test device for detecting an antibiotic in a sample, said test device having a proximal and a distal end, said test device configured to allow lateral flow of a liquid composition comprising a liquid sample, a labeled antibiotic binding protein and a labeled control reagent from the proximal to the distal end, said device comprising a solid support comprising the following regions in sequence from the proximal to the distal end:
      i. a sample receiving region,
      ii. a detection region, said detection region comprising at least two zones:
         A. a detection zone comprising an immobilized antibiotic capable of binding the labeled antibiotic binding protein, when said labeled antibiotic binding protein is unbound by antibiotic from the sample, and
         B. a control zone comprising an immobilized binding agent capable of binding the labeled control reagent,
      iii. an absorbing region, and
      iv. optionally, a handling region.

* * * * *